United States Patent [19]

Beuscher et al.

[11] Patent Number: 5,151,498

[45] Date of Patent: Sep. 29, 1992

[54] **GLYCOPROTEIN FROM *AVENA SATIVA*, PROCESS FOR ITS PREPARATION, AND PHARMACEUTICAL COMPOSITIONS CONTAINING SAME**

[75] Inventors: Norbert Beuscher, Salzgitter Bad; Karl-Heinz Scheit, Goettingen, both of Fed. Rep. of Germany

[73] Assignee: Schaper & Bruemmer GmbH & Co. KG, Salzgitter, Fed. Rep. of Germany

[21] Appl. No.: 515,517

[22] Filed: Apr. 30, 1990

[30] Foreign Application Priority Data

Apr. 29, 1989 [DE] Fed. Rep. of Germany ....... 3914354

[51] Int. Cl.$^5$ ............ A61K 37/02; C07K 3/02; C07K 15/10; C07K 15/14
[52] U.S. Cl. ............................................. 530/372
[58] Field of Search ............... 514/8; 530/395, 372

[56] References Cited

U.S. PATENT DOCUMENTS 2,366,952 1/1945 Balls et al. ........................ 530/372
4,169,090 9/1979 Murray et al. .................... 530/372

Primary Examiner—Jeffrey E. Russel
Attorney, Agent, or Firm—Foley & Lardner

[57] ABSTRACT

A glycoprotein with a molecular weight of 38 kD, isolated from the grain of *Avena sativa*, exhibits surprising pharmacological properties, including immunomodulating activity. The glycoprotein can be used to treat viral and bacterial infections, and can also be used to counter susceptibility to infection arising from a genetic or temporary immunodeficiency. A process for isolating the glycoprotein from *Avena sativa* is disclosed.

21 Claims, 3 Drawing Sheets

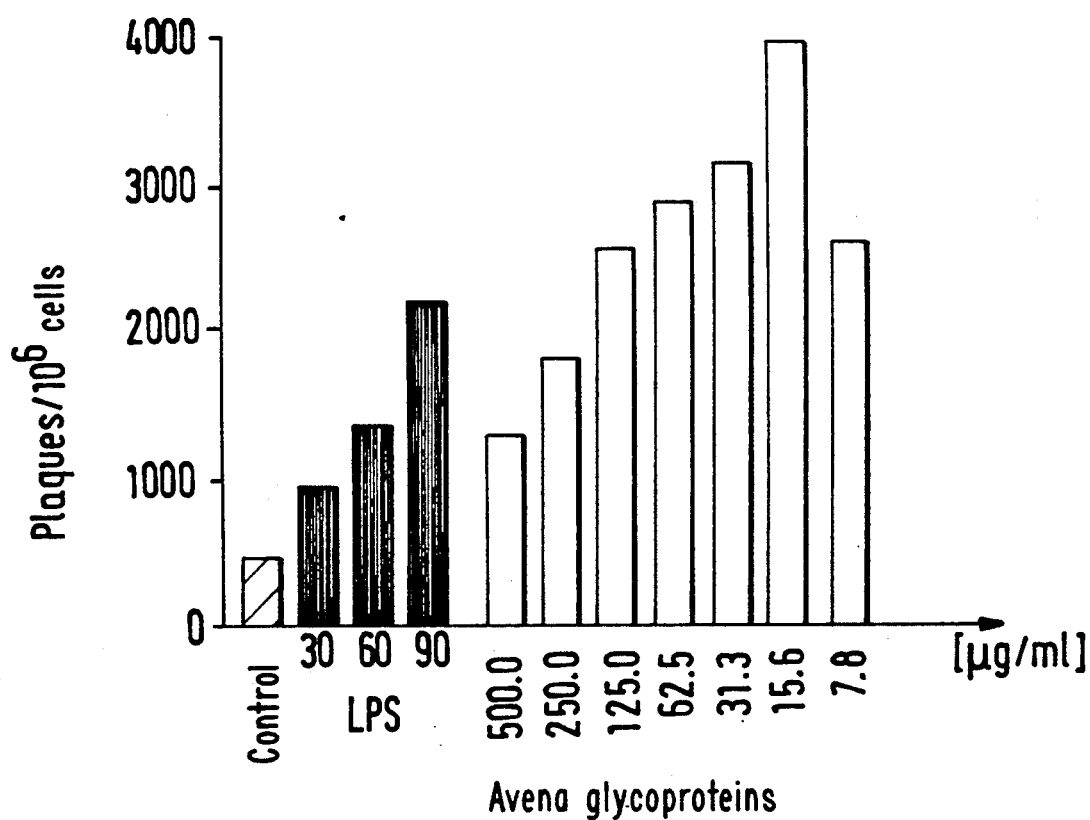

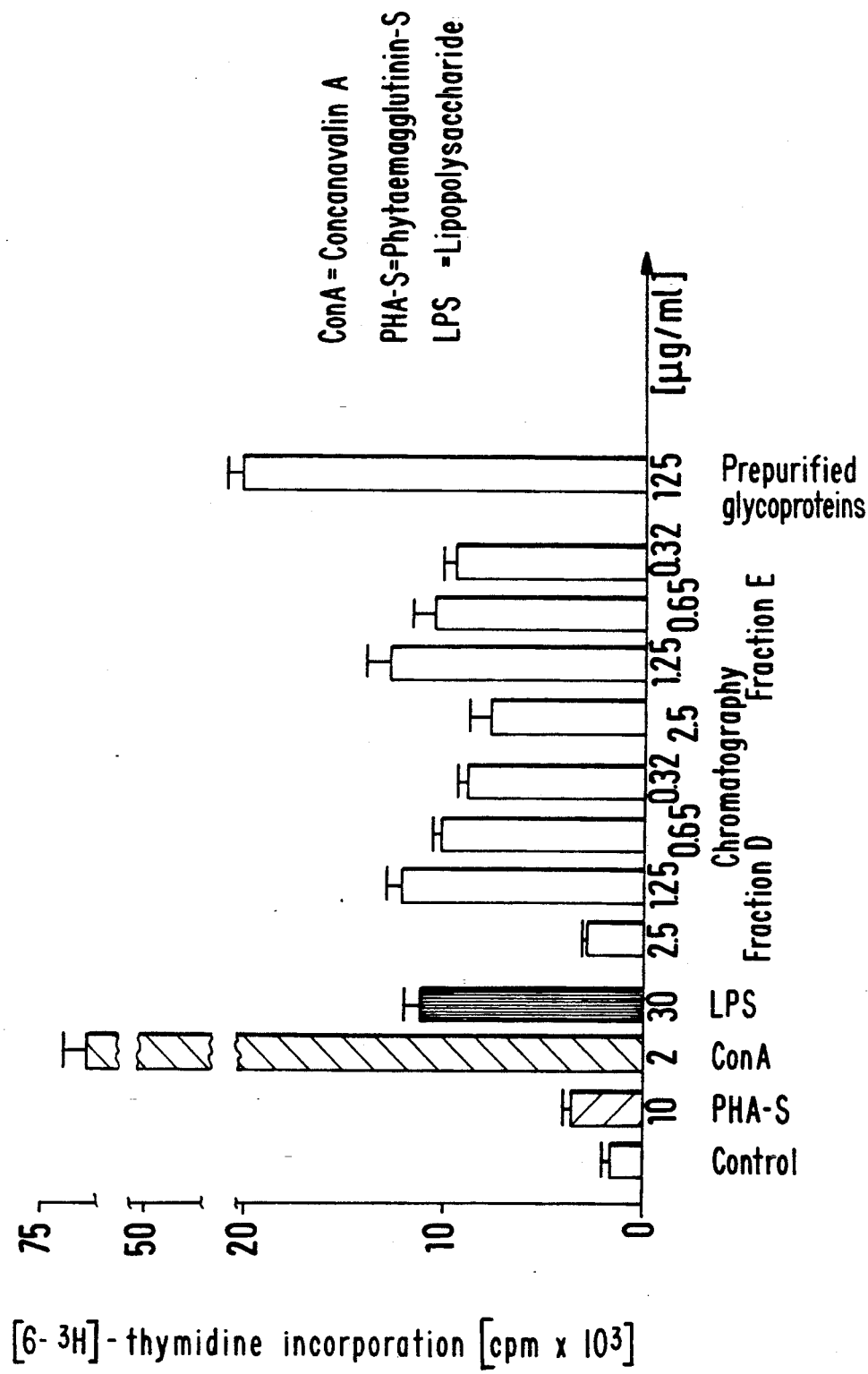

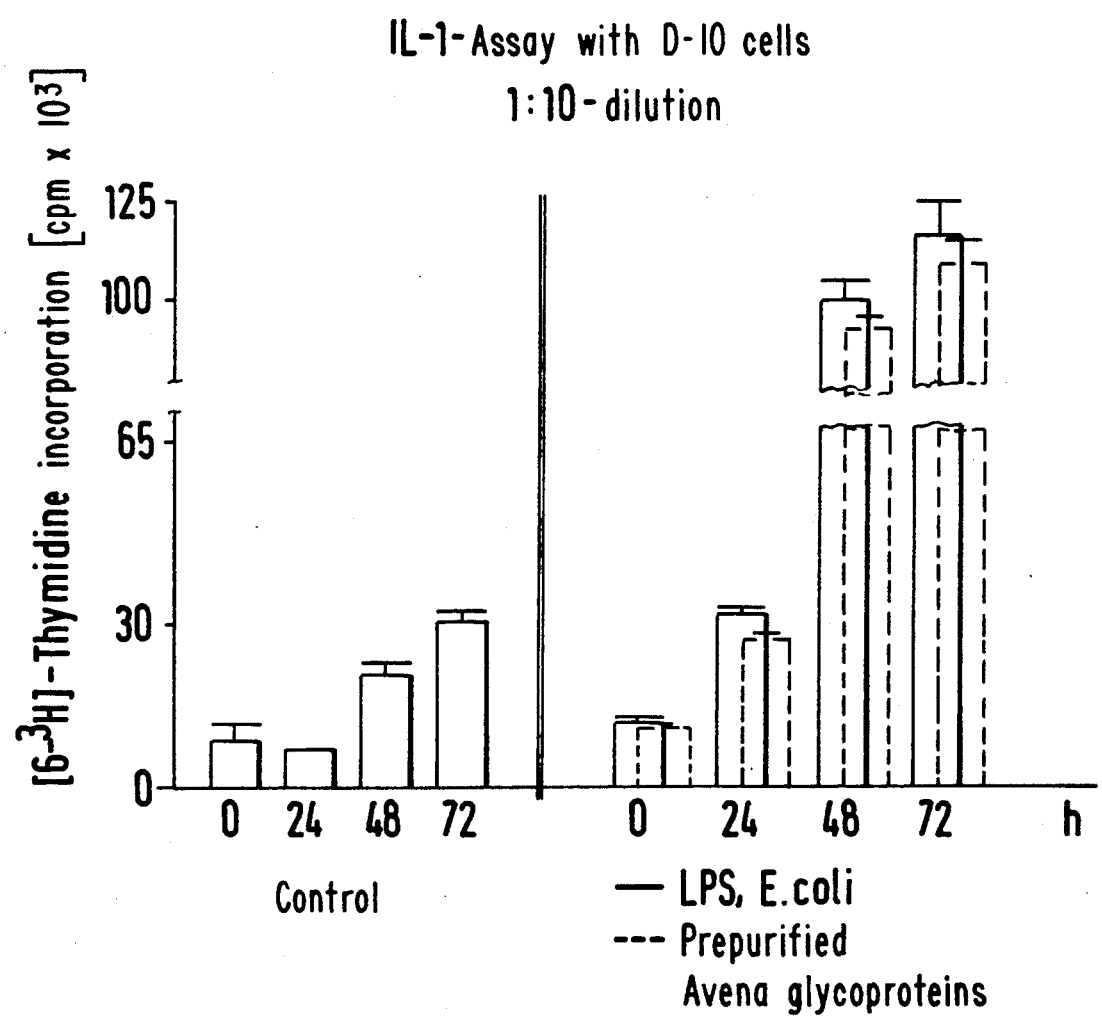

GLYCOPROTEIN FROM *AVENA SATIVA*, PROCESS FOR ITS PREPARATION, AND PHARMACEUTICAL COMPOSITIONS CONTAINING SAME

BACKGROUND OF THE INVENTION

The present invention relates to a glycoprotein. More particularly, it relates to a pharmaceutically-active glycoprotein, having a molecular weight of 38 kD, which can be obtained in substantially pure form from an extract of the grain of *Avena sativa* (oat). The invention also relates to a process for the preparation of such an active glycoprotein and to an immunomodulating pharmaceutical composition containing the glycoprotein as an active ingredient, which composition is useful in the prevention and treatment of viral and bacterial infections.

Glycoprotein fractions from the bacterium *Klebsiella pneumoniae*, having molecular weights ranging from 95 to 350 kilodaltons (kD), have been used to treat patients suffering from chronic bronchitis. Administration of 2 to 8 mg of these glycoprotein extracts improved the antimicrobial activity of monocytes in these patients, and appeared to prevent superinfection.

Bacteria possess several disadvantages as a source of pharmaceutically-active proteins. In particular, purification of proteins from a fermentation medium must be rigorous, in order to prevent the possibility of side effects from substances in the medium, for example, lipopolysaccharides. Isolation of a protein from plant tissue reduces the risks of side effects, and generally provides a more inexpensive source material.

SUMMARY OF THE INVENTION

It is an object of the present invention to provide a glycoprotein useful in immunomodulating pharmaceutical compositions that can be obtained inexpensively from plant tissue.

It is another object of the invention to provide a pharmaceutical composition containing such a glycoprotein, which is useful in the treatment and prevention of viral and bacterial infections.

These and other objects according to the invention are provided by an *Avena sativa* glycoprotein in substantially pure form that has a molecular weight of 38 kD and that displays mitogenic activity. An immunomodulating pharmaceutical composition comprising a pharmaceutically-active amount of the glycoprotein and a pharmaceutically-acceptable excipient is provided. Administration of a pharmaceutically-effective dose of this pharmaceutical composition can be used to treat viral and bacterial infections.

The present invention provides a process for the preparation of the glycoprotein, comprising the steps of grinding grain of *Avena sativa*, extracting a glycoprotein from the ground grain, removing high molecular weight constituents from the extract by filtration, precipitating the high molecular weight constituents, dissolving the precipitate and removing contaminating salts from the solution by dialysis, separating the components into fractions according to molecular weight, and isolating the 38 kD molecular weight fraction.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 presents bar charts detailing the effects of various levels of a glycoprotein according to the invention, as well as the effects of various levels of lipopolysaccharide from E. coli, on immunomodulating activity as assessed by the Jerne plaque test.

FIG. 2 presents bar charts showing the mitogenic activity of a glycoprotein according to the present invention.

FIG. 3 depicts bar charts that demonstrate the ability of a glycoprotein of the present invention to induce interleukin-1.

DESCRIPTION OF THE PREFERRED EMBODIMENTS

A glycoprotein according to the present invention is formed of a polypeptide chain coupled to a polysaccharide, is water-soluble, and has a molecular weight of 38 kD. The molecular weight of such a glycoprotein can be readily determined, in conventional fashion, from an analysis of constituent amino acids and sugars. The molecular weight of the polypeptide chain (that is, of the amino acid residues only) comprising an inventive glycoprotein is 22.2 kD.

The content of amino acid residues is 58.4% for a glycoprotein of the present invention, while the content of sugar residues is 41.6%. The polysaccharide portion of an inventive glycoprotein comprises a neutral hexose component having 45% glucose, 8% galactose, 31% mannose and 15% arabinose. The content of osamines (glucosamine and galactosamine) is below 0.1%. These values can be determined by gas chromatography and amino acid analysis of total hydrolysates.

The amino acid ratios for the protein portion of a glycoprotein according to the present invention are 0.97 for aspartate to glutamate, 1.03 for alanine to valine, 10.6 for valine to histidine, 2.3 for valine to lysine and 3.5 for valine to arginine. The protein portion of an inventive glycoprotein is composed of about 11 mol % aspartic acid, 11 mol % glutamic acid and about 8 mol % threonine. The ratio of glucose to galactose is about 6:1, while the mannose:arabinose ratio is approximately 4:2.

A glycoprotein within the present invention can be extracted from the grain of *Avena sativa*. In a preferred embodiment, the grain is floured and an amount of this flour (say, 5 kg) is slowly added to 30% ethanol (60 liters) with continuous stirring. Clods are immediately resolved. The extraction process is then continued for 24 hours at 4° C. When the resulting extract has been removed and dried for several days, a fine, light, odor-free powder (1300 g) is obtained.

This powder can be dissolved in water and filtered through a hollow-fiber membrane with a high molecular-weight exclusion limit which can accommodate the typically high viscosity of the solution. In this regard, an exclusion limit of 10 kD has been found especially suitable for separating the high-molecular-weight fraction. Such a diafiltration is preferably performed over 17 hours at a pressure of about 4.9 to 5.2 bar and a rate of from 235 to 830 ml/hour.

The high molecular weight constituents of the extract are removed by filtration, particularly by diafiltration, for further processing. The dialfiltration membrane used for this retains high molecular weight constituents (>5 kD), and these constituents are then precipitated with a precipitant suitable for glycoproteins, preferably ammonium sulfate. The resulting precipitate is isolated, for example, by centrifugation, dissolved in water and dialyzed in order to remove contaminating salts.

The purified solution is preferably lyophilized for storage and subsequently redissolved. This is followed by separation of the components according to molecular weight ranges. Separation is preferably carried out by a gel chromatography. The mitogenic activity of the fractionated Avena glycoproteins can be determined via a lymphocyte-transformation test using mouse spleen cells, in which incorporation of [6-$^3$H]-thymidine into lymphocyte DNA is measured (see FIG. 2).

When glycoprotein fractions obtained by column gel chromatography, as described above, were compared with bacterial lipopolysaccharide (LPS), a B-cell mitogen, the 38 kD fraction of the present invention effected a stimulation, at a concentration of 1.25 µg/ml, that was equal to the stimulation achieved with 30 µg/ml of LPS. In a similar comparison involving prepurified glycoprotein (a glycoprotein composition that had not been fractionated chromatographically), the 38 kD fraction produced a stimulation, at 1.25 µg/ml, that was 50% of the stimulation obtained with 125 µg/ml of prepurified glycoprotein.

The 38 kD fraction elutes as a sharp peak and is amenable to amino-acid analysis, indicating that the constituent glycoprotein is in substantially pure form. (This can be proved by conventional sodium-dodecyl sulphate electrophoresis, whereby 38 kD glycoprotein of the present invention migrates as a single band.) The fraction can be concentrated and, where appropriate, lyophilized again.

It may be advantageous, before carrying out the process according to the present invention, to remove high molecular weight contaminating substances such as lipids and nucleic acids from the extract. It is possible for this purpose to carry out a precipitation with quaternary ammonium, for example, with pyridylcetylammonium chloride, but preferably trimethylcetylammonium bromide. Subsequent centrifugation separates out the precipitated concomitants. For stability reasons, the precipitations and centrifugations are preferably carried out in the cold (at about +4° C.).

Pursuant to the present invention, diafiltration is performed with membranes of defined pore size which retain molecules having a molecular weight above a given value. These membranes can be hollow-fiber cartridges, but the use of spiral ultrafiltration units is preferred. Commercially-available Millipore PTGC membranes are preferably used. The selection of the molecules with a molecular weight exceeding a given molecular weight can, of course, also be carried out by other processes, such as, for example, chromatography on a hydrophilic polymerized gel.

Hydrophilic polymerized gels having an exclusion volume greater than about 30 kD that are formed from modified dextrans are preferably used for the separation of the components according to molecular weights. Gels commercially available under the name "Sephadex G-50" are suitable.

The fractions that are eluted first are combined, concentrated and dialyzed. This is followed by evaporation to dryness, which is advantageously carried out by freeze-drying. The lyophilizations are carried out in the known manner using freeze-sublimation systems which are commercially available in average size and as small laboratory devices.

Gel filtration is carried out after the lyophilisate has been dissolved. The solution to be filtered is preferably buffered, and the elution is carried out with the same buffer. A 0.1M ammonium carbonate buffer is preferably used. The filtration can be followed using classical methods, especially UV spectroscopy at 280 nm. The gel used for this filtration is preferably a modified dextran, particularly one which is commercially available under the name "Sephacryl S-200."

A glycoprotein according to the present invention has surprising pharmacological properties, including remarkable immunomodulating (lymphocyte-activating) properties, and is well-tolerated. These properties make a glycoprotein of the invention a useful constituent of pharmaceutical compositions. These pharmaceutical compositions are used, for example, in the treatment and prevention of bacterial and viral infections, both acute and chronic, in humans and animals. Examples of bacterial infections which are treatable in this manner are bronchitis, tonsillitis, laryngitis, otitis and sinusitis. Examples of treatable viral infections are those caused by herpes viruses, rhino viruses, influenza viruses, HIV and cytomegaloviruses.

A glycoprotein according to the invention can additionally be employed in countering a susceptibility to infection arising from a genetic or temporary immunodeficiency. The usual dose will vary depending on the patient to be treated and the particular disease requiring therapy. In humans it may be, for example, between 10 and 200 mg per day on oral administration, 1 to 15 mg per day on rectal administration and 2 to 20 mg per day on parenteral administration.

The appropriate pharmaceutical compositions may be solids or liquids in pharmaceutical forms customarily employed in human medicine, such as, for example, coated and uncoated tablets, gelatin capsules, granules, solutions, syrups, suppositories, injectable, lyophilized or non-lyophilized products, pessaries, creams, lotions, drops, eye drops, aerosols, and they can be prepared by customary methods. The active ingredient or ingredients can be incorporated in the excipients customarily used in pharmaceutical compositions of these types, such as talc, gum arabic, lactose, starch, magnesium stearate, cocoa butter, aqueous or non-aqueous vehicles, fats of animal or vegetable origin, paraffin derivatives, glycols, various wetting, dispersing or emulsifying agents and preservatives.

The following examples of pharmaceutical preparations comprising the glycoproteins are provided to further illustrate the invention.

1. Tablets Containing Avena Glycoproteins

Required for the preparation of tablets each weighing 200 mg and containing 50 mg of glycoproteins are:
Avena glycoproteins: 50 mg
Microcrystalline cellulose e.g. "Avicel ph 102": 129 mg
Polyvinylpyrrolidone (e.g. "Polyplasdone XL"): 20 mg
Magnesium stearate: 1 mg 2. Capsules Containing Avena Glycoproteins Required for a 300 mg capsule are:

Avena glycoproteins: 50 mg
Yellow beeswax: 10 mg
Soybean oil: 10 mg
Vegetable oil: 130 mg
Capsule shell: 100 mg

3. Solution Containing Avena Glycoproteins

Required for 100 ml are:
Avena glycoproteins: 500 mg
Sorbitol: 10 g
Sodium saccharin: 0.05 g
Double-distilled H$_2$O: to 100 ml

4. Injection Ampoules Containing Avena Glycoproteins

Required for the preparation of injection ampoules, each containing 2 ml that contains 2 mg of glycoproteins are:
Avena glycoproteins: 2 mg
Physiological NaCl: to 2.0 ml

5. Infusion Solution Containing Avena Glycoproteins

Required for 500 ml of infusion solution are:
Avena glycoproteins: 20 mg
Physiological NaCl: to 500 ml

6. Ointment Containing Avena Glycoproteins

Required for 100 g of ointment are:
Avena glycoproteins: 1 g
Mixture of cetylstearyl alcohol and sodium cetylstearyl sulfate and emulsifier (e.g., "Emulgade F"): 17 g
Decyl oleate (e.g., "Cetiol V"): 20 g
Mixture of p-hydroxybenzoic esters and sorbic acid (e.g., Nipasorbin): 0.5 g
Double-distilled H$_2$O: 61.5 g Pharmacological investigations of the stimulation of immunological defense reactions were carried out to test immunomodulating activity and interleukin-1 induction.

Immunomodulating activity was tested by means of the ability to stimulate the formation of antibodies by mouse lymphocytes. In a Jerne antibody plaque test, well-known to those skilled in the art, the Avena glycoproteins were able to bring about a highly significant increase in the syntheses of antibodies against sheep erythrocytes (FIG. 1). The stimulation was a maximum at a concentration of 15.6 $\mu$g/ml and was about eight times that of an untreated control. Compared with a known stimulant, *Escherichia coli* LPS, the stimulation at comparable concentrations of 60 and 30 $\mu$g/ml respectively was two to three times as high.

Interleukin-1 is an immunologically non-specific cytokine which functions as a central mediator of the body's defenses. Because of its properties of activating lymphocytes, modulating the expression of acute-phase proteins and inducing fever, interleukin-1 has prominent significance in the area of inflammation and of infection. Monocytes and macrophages are the predominant producers of interleukin-1. As a consequence, the test was carried out on a macrophage line (FIG. 3). In an interval of 72 hours, Avena glycoproteins bring about a stimulation which is approximately equal to that of *Escherichia coli* LPS which is known to induce interleukin-1 secretion. The concentration of prepurified glycoproteins was 60 $\mu$g/ml, and for the lipopolysaccharide it was 10 $\mu$g/ml. By contrast, an untreated control achieved only one third of the incorporation rate in 72 hours.

What is claimed is:

1. An *Avena sativa* glycoprotein that migrates as a single band during SDS electrophoresis, said glycoprotein having a molecular weight of 38 kD and mitogenic activity.

2. A glycoprotein as claimed in claim 1, wherein the glycoprotein has amino acid ratios of 0.97 for aspartate to glutamate, 1.03 for alanine to valine, 10.6 for valine to histidine, 2.3 for valine to lysine and 3.5 for valine to arginine.

3. A glycoprotein as claimed in claim 2, wherein said glycoprotein comprises a 22.2 kD polypeptide chain.

4. A glycoprotein as claimed in claim 1, wherein said glycoprotein comprises a neutral hexose component having 45% by weight glucose, 8% by weight galactose, 31% by weight mannose and 15% by weight arabinose and an osamine content below 0.1% by weight.

5. A glycoprotein as claimed in claim 4, comprising 58.4% by weight amino acid residues and 41.6% by weight sugar residues.

6. A glycoprotein as claimed in claim 1, wherein said glycoprotein contains a polypeptide portion comprised of 11 mol % aspartic acid, 11 mol % glutamic acid and 8 mol % threonine.

7. A glycoprotein as claimed in claim 1, comprising glucose to galactose ratio of 6:1 and a mannose to arabinose ratio of 4:2.

8. A process for the preparation of a glycoprotein, comprising the steps of:
grinding grain of *Avena sativa*;
extracting a glycoprotein from the ground grain;
removing constituents having a molecular weight greater than about 5 kD from the extract by filtration;
precipitating the constituents having a molecular weight greater than about 5 kD;
dissolving the precipitate and removing contaminating salts from the solution by dialysis;
separating the components into fractions according to molecular weight; and
isolating the 38 kD molecular weight fraction.

9. A process as claimed in claim 8, wherein the removal by filtration of the constituents having a molecular weight greater than about 5 kD is carried out by diafiltration.

10. A process as claimed in claim 8, wherein ammonium sulfate is used as precipitant.

11. A process as claimed in claim 8, additionally comprising the step of lyophilizing the dialysis product.

12. A process as claimed in claim 8, wherein the separation of the components according to molecular weight ranges is carried out by a gel chromatography.

13. A process as claimed in claim 12, wherein the chromatography solution is buffered, and elution is carried out with the same buffer.

14. A process as claimed in claim 13, wherein 0.1M ammonium carbonate buffer is used.

15. A process as claimed in claim 8, additionally comprising a step of precipitating and removing lipids and nucleic acids from the extract before the step of removing constituents having a molecular weight greater than about 5 kD from the extract by filtration.

16. A process as claimed in claim 15, wherein quaternary ammonium is used for precipitation of the lipids and nucleic acids.

17. An *Avena sativa* glycoprotein having a molecular weight of 38 kD, said glycoprotein being obtained by a process comprising the steps of:
   grinding grain of *Avena sativa*;
   extracting a glycoprotein from the ground grain;
   removing constituents having a molecular weight greater than about 5 kD from the extract by filtration;
   precipitating the constituents having a molecular weight greater than about 5 kD;
   dissolving the precipitate and removing contaminating salts from the solution by dialysis;
   separating the components into fractions according to molecular weight; and
   isolating the 38 kD molecular weight fraction.

18. A glycoprotein as claimed in claim 17, wherein the process of isolating said glycoprotein additionally comprises a step of precipitating and removing lipids and nucleic acids from the extract before the step of removing constituents having a molecular weight greater than about 5 kD from the extract by filtration.

19. A glycoprotein as claimed in claim 17, wherein the glycoprotein has amino acid ratios of 0.97 for aspartate to glutamate, 1.03 for alanine to valine, 10.6 for valine to histidine, 2.3 for valine to lysine and 3.5 for valine to arginine.

20. A glycoprotein as claimed in claim 17, wherein said glycoprotein comprises a 22.2 kD polypeptide chain.

21. A glycoprotein as claimed in claim 20, wherein said polypeptide chain comprises 11 mol % aspartic acid, 11 mol % glutamic acid and 8 mol % threonine.

* * * * *